United States Patent [19]

Paciello

[11] Patent Number: 5,180,870
[45] Date of Patent: Jan. 19, 1993

[54] HYDROGENATION OF POLYENES

[75] Inventor: Rocco A. Paciello, Wilmington, Del.

[73] Assignee: E. I. du Pont de Nemours and Company, Wilmington, Del.

[21] Appl. No.: 781,361

[22] Filed: Oct. 23, 1991

[51] Int. Cl.[5] ................................. C07C 5/02
[52] U.S. Cl. ................... 585/277; 585/273; 585/275
[58] Field of Search ..................... 585/277, 273

[56] References Cited

U.S. PATENT DOCUMENTS 3,804,914  4/1974  Fahey .................... 585/273
3,925,494  12/1975  Fahey .................... 585/273

OTHER PUBLICATIONS

Fahey, "Selective Hydrogenation of 1,5,9-Cyclododecatriene . . . " J. Org. Chem. 38(1) pp. 80-87 (1973).

Nishimura et al., "Selective Homogeneous Hydrogenation of 3-Oxo-, 4-diene Steroids II. Effects . . . " Bull. Chem. Soc. Japan (46) pp. 279-283 (1973).

Bulletin of the Chemical Society of Japan, vol. 46, 279-282 (1973), "Selective Homogeneous Hydrogenation of 3-Dxo-1,4-diene Steroids II" by Nishimura et al.

J. Am. CHem. Soc., 1991, vol. 113, pp. 2520-2527, "Cone Angles for Amine Ligands" by Seligson et al.

Primary Examiner—Anthony McFarlane
Assistant Examiner—C. Everhart
Attorney, Agent, or Firm—Earl L. Handley

[57]  ABSTRACT

Hydrogenation of a polyene to a monoene using a ruthenium catalyst that is promoted with a sterically-hindered tertiary amine.

5 Claims, No Drawings

HYDROGENATION OF POLYENES

FIELD OF THE INVENTION

This invention relates to the hydrogenation of a polyene to produce a monoene using a ruthenium catalyst that is promoted by a sterically-hindered tertiary amine or a sterically-hindered pyridine.

BACKGROUND OF THE INVENTION

The hydrogenation of polyenes to produce monoenes using ruthenium complex catalysts is disclosed in Fahey's U.S. Pat. No. 3,925,494. Fahey's U.S. Pat. No. 3,804,914, in Example II shows hydrogenation of polyenes using a ruthenium complex catalyst and excess triphenylphosphine. Fahey discloses in Journal of Organic Chemistry, Vol. 38, No. 1, 1973, pages 80-87 that Lewis Bases, including diethylamine were tested in the hydrogenation of cyclododecatriene. No bases were found to be more effective at enhancing selectivity than triphenylphosphine. No other effects were noted.

The rate of hydrogenation of a particular polyene using a ruthenium catalyst is taught to be increased by adding certain specific amines in an article titled "Selective Homogeneous Hydrogenation of 3-Oxo-1,4-diene Steroids. II. Effects of Basic Additives and para Substituents on the Hydrogenation with Dichlorotris(triphenylphosphine) ruthenium", by Nishimura et al, appearing in Bulletin of the Chemical Society of Japan, Vol. 46, 279-283 (1973).

The process disclosed by the Fahey patents suffers from the difficulty that there is an induction period of considerable length between the time the ingredients of the reaction mixture are combined under reaction conditions, and the time that the mixture actually begins to react at a significant rate.

An object of the present invention is to shorten this induction period.

SUMMARY OF THE INVENTION

The present invention is a process for the hydrogenation of a polyene to a monoene which comprises forming a reaction mixture containing the polyene, hydrogen, a ruthenium-ligand complex hydrogenation catalyst, free triarylphosphine, and a sterically-hindered tertiary amine of the formula $NR_3$ where R is alkyl or aryl or a sterically-hindered pyridine having an alkyl or aryl substitutent in the 2 and/or 6 position, and reacting the mixture under hydrogenation conditions. The presence of the sterically-hindered tertiary amine or pyridine promotes the reaction, i.e., it reduces the induction period. Preferred sterically-hindered tertiary amines have cone angles of greater than 200 degrees. The term "cone angle" is used in accordance with the Seligson et al. article, J. Am. Chem. Soc., 1991, Vol. 113, No. 7, page 2520. Cone angle describes the amount of space taken up by a particular amine ligand on the metal i.e., ruthenium atom.

DETAILED DESCRIPTION

It is preferred that the ruthenium-ligand complex hydrogenation catalyst have the formula: $Ru(PAr_3)_2(CO)_2Cl_2$ (in which the triarylphosphine ligand $P(Ar)_3$ is from the group consisting of $P(C_6H_5)_3$, $P(p\text{-tolyl})_3$, $P(p\text{-F-}C_6H_4)_3$, $P(p\text{-OMe-}C_6H_4)_3$ or $P\text{-}(p\text{-F-}(C_6H_5)_3)$ The process is particularly effective in converting cyclododecatriene to cyclododecene.

The preferred sterically-hindered tertiary amines are those in which the R groups have 2 to 18 carbon atoms, and in which the total number of carbon atoms on all R groups is between 7 and 48. The preferred stericallyhindered pyridines are those in which the alkyl groups have 1 to 18 carbon atoms, or aryl groups having 6 to 14 carbon atoms. Examples are ethyldiiso-propylamine, tritolueneamine, N,N,N,N-tetramethyethylene-diamine, and 2,6-di-tert-butyl-4-methylpyridine. The tertiary amines may be used in lieu of other promoters such as lithium aluminum hydride, water, water-containing basic compounds like sodium hydroxide, or calcium carbonate. Normally the amount of sterically-hindered tertiary amine or pyridine in the reaction mixture should be in the amount of about 2 to 10 moles per mole of catalyst.

The amount of free triarylphosphine present in the reaction mixture should normally be in the range of about 5 to 50 moles per mole of catalyst. Suitable triarylphosphines include: triphenylphosphine, tris-paratolylphosphine, tris-para-fluorophenylphosphine, tris-para-methoxyphenylphosphine. It is desirable that the excess triarylphosphine be the same compound as the phosphine ligand on the ruthenium catalyst.

The amount of catalyst in the reaction mixture may vary widely, but is usually in the range set forth in the Fahey patent 3,925,494, i.e., 0.00001 to about 0.5 mole of ruthenium-ligand complex per mole of polyene. In addition to 1,5,9-cyclododecatriene the process operates on 1,5-cyclooctadiene, and linoleic acid ethyl ester. The Fahey patent ,494 indicates that such catalysts are satisfactory for cyclic and acyclic polyenes of up to 20 carbon atoms including 1,3-cyclopentadiene, 1,3-pentadiene, and 1,3,7,9-octa-decatetraene.

The process is normally operated at a pressure in the range of about 100 to about 600 psi and at a temperature in the range of about 130 to about 150° C.

Suitable solvents include benzene, toluene, cumene, isooctane, cyclohexane, ethanol, 1-butanol, ethylacetate, tetrahydrofuran. The reaction can be conducted without a solvent.

EXAMPLES

Table 1 below sets forth the ingredients, the amounts of the ingredients, and the results obtained when the reaction is run in a quartz Fischer-Porter tube at 120 psi $H_2$ and 150° C. All of the catalysts had the form $Ru(PAr_3)_2(CO)_2Cl_2$. The percent conversion is after 4 hours.

TABLE I

| | Pu Complex (mg) | CDDT (ml) | PAr₃** (g) | Promotor | NR₃ | Toluene (ml) | % Conv (4 h) |
|---|---|---|---|---|---|---|---|
| Control 1 | PPh₃ 50 mg | 12 | 1.102 | — | — | 8 | 7% |
| Control 2 | PPh₃ 50 mg | 12 | 1.102 | LiAlH₄ 2.5 mg | — | 8 | 11.9 |
| Example 1 | PPh₃ 50 mg | 12 | 1.102 | LiAlH₄ 2.5 mg | 60 μL NEt(i-Pr)₂ | 18 | 47.5 |
| Example 2 | PPh₃ 50 mg | 12 | 1.102 | LiAlH₄ 2.5 mg | 95 mg (N)(CH₂Ph)₃ | 15 | 37.9 |
| Example 3 | PPh₃ 50 mg | 12 | 1.18 | — | 50 μL NEt(i-Pr)₂ | 15 | 85.9 |
| Example 4 | PPh₃ 50 mg | 12 | 1.18 | — | 68 μL 2,5-di-tert- | 18 | 56.3 |

TABLE I-continued

| | Pu Complex (mg) | CDDT (ml) | PAr₃** (g) | Promotor | NR₃ | Toluene (ml) | % Conv (4 h) |
|---|---|---|---|---|---|---|---|
| Example 5 | PPh₃ 50 mg | 12 | 1.18 | — | butyl-4-methylpyridine 71 mg* | 15 | 32.8 |
| Example 6 | PPh₃ 50 mg | 12 | 1.18 | — | 14 mg* | 15 | 32 |
| Example 7 | PPh₃ 50 mg | 12 | 1.18 | — | 46 L TMEDA** | 15 | 76.5 |
| Example 8 | PPh₃ 50 mg | 12 | 1.18 | — | 46 L NEt₃ | 15 | 25 |
| Example 9 | PPh₃ 50 mg | 12 | 1.18 | — | 27 L Pyridine | 15 | 2.2 |
| Example 10 | P(p-F—C₆H₄) | 11.3 | 0.196 | — | 54 μL NEt(i-Pr)₂ | 8.7 | 92.7 |
| Example 11 | P(p-F—C₆H₄)₃ | 11.3 | 0.196 | — | — | 18.7 | 8.6 |
| Example 12 | P(p-OMe—C₆H₄)₃ | 10.8 | 0.209 | — | 52 μL NEt(i-Pr)₂ | 19.2 | 55.4 |
| Example 13 | P(p-OMe—C₆H₄)₃ | 10.8 | 0.209 | — | — | 19.2 | 22.7 |
| Example 14 | PPh₂(p-Me—C₆H₄) | 11.9 | 1.18 | — | 57 μL NEt(i-Pr)₂ | 18.1 | 93.9 |
| Example 15 | PPh₂(p-Me—C₆H₄) | 11.9 | 1.18 | — | — | 18.1 | 64.2 |
| Control 3 | PPh₃ 50 mg | 12 | 1.18 | 50 μL H₂O | — | 18 | 2.0 |
| Control 4 | PPh₃ 50 mg | 12 | 1.18 | 50 μL 10%/NaOH aq | — | 18 | 1.9 |
| Control 5 | PPh₃ 50 mg | 12 | 1.18 | 50 μL H₂O/7 mg CaCO₃ | — | 18 | 2.8 |

*1,-8-bis(dimethylamino)napthalene
**N,N,N,N-tetramethylethyldiamine
***Triphenylphosphine Table 2 below sets forth the ingredients, the amount of ingredients, and the results obtained when the reaction is run in a Fischer-Porter tube at 150° C. and at 500 psi. All catalysts had the form Ru(PAr₃)₂(CO)₂Cl₂.

TABLE 2

| | Ru complex (mg) | CDDT (ml) | PAr₃* (g) | Promoter | NR₃ | % Conv (4 H) |
|---|---|---|---|---|---|---|
| Control | PPh₃ 25 mg | 32 | 0.174 | — | — | 2.8 |
| Example 16 | PPh₃ 25 mg | 32 | 0.174 | — | 29 1 NEt(i-Pr)₂ | 24.2 |
| Control 8 | PPh₃ 25 mg | 32 | 0.174 | — | 9 1 NEt₃ | 2.9 |

*Triphenylphosphine

I claim:

1. A process for the hydrogenation of a polyene to a monoene which comprises forming a reaction mixture containing the polyene, hydrogen and a ruthenium-ligand complex hydrogenation catalyst, Ru(PAr₃)₂(CO)₂Cl₂ in which the triarylphosphine ligand P(Ar)₃ is selected from the group consisting of P(p-tolyl)₃, P(p-F-C₆H₄)₃, P(p-OMe-C₆H₄)₃ or P(C₆H₅)₃, free triarylphosphine and a sterically-hindered tertiary amine promoter of the formula NR₃, where R is alkyl or aryl or a sterically-hindered pyridine having alkyl or aryl groups in the 2 and/or 6 position, and reacting the mixture under hydrogenation conditions, said sterically-hindered tertiary amine or said sterically-hindered pyridine being present in the reaction mixture in an amount in the range of 2 to 10 moles per mole of catalyst.

2. A process for the hydrogenation of cyclododecatriene to cyclododecene which comprises forming a reaction mixture containing cyclododecatriene, hydrogen, and a ruthenium-ligand complex hydrogenation catalyst having the formula: Ru(PPh₃)₂)(CO)₂Cl₂, free triphenyl phosphine and a sterically-hindered tertiary amine promoter of the formula: NR₃, where R is aklyl or aryl, and reacting the mixture under hydrogenation conditions, said sterically-hindered tertiary amine promoter being present in the reaction mixture in amount in the range of 2 to 10 moles per mole of catalyst.

3. The process of claim 2 in which the promoter is ethyldiisopropylamine.

4. The process of claim 3 in which the reaction is carried out at a pressure in the range of about 100 to about 600 psi, and at a temperature in the range of about 130 to about 150 degrees C.

5. The process of claim 2 in which the amount of free triarylphosphine present in the reaction mixture is in the range of about 5 to 50 moles per mole of catalyst.

* * * * *